(12) United States Patent
Rosero et al.

(10) Patent No.: US 12,035,994 B2
(45) Date of Patent: Jul. 16, 2024

(54) IMPLANTABLE DEVICES AND METHODS OF USE

(71) Applicant: EFFERENT LABS, INC., Buffalo, NY (US)

(72) Inventors: Spencer Z. Rosero, Pittsford, NY (US); William K. Rader, Huger, SC (US)

( * ) Notice: Subject to any disclaimer, the term of this patent is extended or adjusted under 35 U.S.C. 154(b) by 162 days.

(21) Appl. No.: 16/410,294

(22) Filed: May 13, 2019

(65) Prior Publication Data

US 2019/0350458 A1    Nov. 21, 2019

Related U.S. Application Data (60) Provisional application No. 62/671,455, filed on May 15, 2018.

(51) Int. Cl.
*A61B 5/00* (2006.01)
*A61B 5/01* (2006.01)
*A61B 5/021* (2006.01)
*A61B 5/145* (2006.01)
(Continued)

(52) U.S. Cl.
CPC .......... *A61B 5/0031* (2013.01); *A61B 5/0017* (2013.01); *A61B 5/01* (2013.01); *A61B 5/021* (2013.01); *A61B 5/14532* (2013.01); *A61B 5/14546* (2013.01); *A61B 5/318* (2021.01);
(Continued)

(58) Field of Classification Search
CPC ......... A61B 5/01; A61B 5/021; A61B 5/0402; A61B 5/145; A61B 5/14532; A61B 5/14503; A61B 5/14546; A61B 5/0024; A61B 5/0031; A61B 5/0205; A61B 5/318; A61B 5/6861; A61B 5/0017; A61B 5/024;
(Continued)

(56) References Cited

U.S. PATENT DOCUMENTS

| | | | |
|---|---|---|---|
| 5,713,888 A * | 2/1998 | Neuenfeldt | A61F 2/022 604/890.1 |
| 6,673,596 B1 * | 1/2004 | Sayler | G01N 33/84 435/288.7 |

(Continued)

FOREIGN PATENT DOCUMENTS

| | | |
|---|---|---|
| EP | 2487248 A1 | 8/2012 |
| WO | 2017/136790 A1 | 8/2017 |

OTHER PUBLICATIONS

International Search Report and Written Opinion of the International Searching Authority dated Jul. 25, 2019, International Application No. PCT/US2019/031977, pp. 1-13.

(Continued)

*Primary Examiner* — Eric J Messersmith
(74) *Attorney, Agent, or Firm* — BioPharma Law Group, PLLC; Joanna T. Brougher, Esq.

(57) ABSTRACT

An implantable device for monitoring physiological changes in a patient is provided. The device can include a vessel adapted to being implanted within a patient's body; a chamber having a cell layer and capable of being secured to the vessel; a light source for shining light onto the cell layer; and a reader for detecting and/or decoding signals from the cell layer to monitor physiological changes in the patient. The device is capable of engaging in a two-way communication with a second device through transmission of one or more electromagnetic signals through at least a portion of the patient's body.

33 Claims, 9 Drawing Sheets

(51) Int. Cl.
*A61B 5/318* (2021.01)
*A61L 27/36* (2006.01)

(52) U.S. Cl.
CPC ........ *A61B 5/6861* (2013.01); *A61L 27/3604* (2013.01)

(58) Field of Classification Search
CPC ..... A61B 5/283; A61B 5/02154; A61L 27/36; A61L 27/3604
See application file for complete search history.

(56) References Cited

U.S. PATENT DOCUMENTS

| | | | |
|---|---|---|---|
| 7,163,825 B2* | 1/2007 | Gault | C12M 35/04 435/401 |
| 7,892,222 B2* | 2/2011 | Vardi | A61F 2/022 604/93.01 |
| 8,938,300 B2* | 1/2015 | Rosero | A61N 1/372 607/45 |
| 2006/0252976 A1 | 11/2006 | Rosero | |
| 2010/0202966 A1* | 8/2010 | Gross | A61B 5/14556 424/9.1 |
| 2012/0041289 A1* | 2/2012 | Rosero | A61N 1/372 600/431 |
| 2018/0050154 A1* | 2/2018 | Cahan | A61M 5/142 |
| 2018/0085038 A1* | 3/2018 | Chen | A61B 5/14503 |

OTHER PUBLICATIONS

Partial Supplementary European Search Report dated Sep. 8, 2022, European Application No. 19803593.3, pp. 1-13.
Notice of Reasons for Rejection dated Jun. 20, 2023, Japanese Patent Application No. 2021-514287, pp. 1-15.

* cited by examiner

CytoComm Body

CytoComm Lid

IMPLANTABLE DEVICES AND METHODS OF USE

RELATED APPLICATIONS

This application claims the benefit of U.S. Provisional Application No. 62/671,455, filed May 15, 2018, the entire contents of which are incorporated herein by reference.

FIELD OF THE INVENTION

The present invention relates to implantable devices suitable for monitoring physiological changes within the body.

BACKGROUND

Generally, wireless communication provides an advantage over lead based systems but also introduces a new technical problem: local noise or motion artifact that can lead or contribute to electromagnetic interference. Wireless systems based on RF are inherently susceptible to environment EMI (electromagnetic interference) and has significant power requirements that limit implantable technology.

The potential problems that patients can experience due to communication interruptions in any implantable cardiac device whether wireless or lead based, include inappropriate shock therapy, unintended inhibition of pacing due to over sensing, commanded therapy signaling may not be received and acted upon, and early battery depletion because of need to repeat transmission or increase power of transmission. The potential issue of wireless communication affecting an unintended patient in the same vicinity as the patient with the device of interest at that time needs to be addressed.

Recent advances allowing the verification and security of data being transmitted to the targeted device have minimized the concern in this area. Pacemaker/ICD programmers have addressed the problem in systems that clinicians use to interrogate pacemakers in the office. If one tries to interrogate a different device when the previous patient's software interface is active, the device does not allow it because it recognizes the different Controller ID during communication. A new link is then required. This encoding can be done at the micro level and provides the safeguards needed. The main technical challenges will involve securing accurate transmission of data between modules including implantable cell based sensors.

Thus, there is a need for a novel system that utilizes at least two (2) and possibly three (3) different media for communication within a single implantable biosensor system.

While the use of RF and ultrasonic communication within or around the body is well established, the invention of the present application uses optical emission that specifically uses the body and its tissues as the medium through which to communicate within the body and the external world as well.

SUMMARY

There is a need for improved implantable devices and methods for monitoring physiological changes a patient. The present invention is directed toward further solutions to address this need, in addition to having other desirable characteristics.

In accordance with an example embodiment of the present invention, an implantable device for monitoring physiological changes in a patient is disclosed. The device can include a vessel adapted to being implanted within a patient's body; a chamber having a cell layer and capable of being secured to the vessel; a light source for shining light onto the cell layer; a reader for detecting and/or decoding signals from the cell layer to monitor physiological changes in the patient.

According to aspects of the present invention, the vessel can be tubular, rectangular, square, or any other shape. The vessel can be adapted to being implanted in each of a intravascular, extravascular, and perivascular space within the patient's body.

In accordance with yet further aspects of the present invention, the chamber comprises a body adapted to being secured to the vessel. The chamber can include a biologic component. The biologic component can include a cell layer having cells pre-positioned on or in the device prior to implantation. The pre-positioned cells can be adapted to respond to a physiological signal from the patient.

In accordance with yet further aspects of the present invention, the chamber can further include a first membrane and a second membrane on either side of the biologic component. The first membrane can be a non-porous membrane on which the cell layer is pre-positioned. The first membrane can be made from glass. The second membrane can be a porous membrane that allows for select fluid and nutrients to pass to the cell layer. The second membrane can be distal to the light source. The light source can shine light onto the cell layer thereby causing certain cells within the cell layer to emit light.

In accordance with yet further aspects of the present invention, the device can be capable of wireless communication. The device can be capable of engaging in a two-way communication through transmission of one of more signals through at least a portion of the patient's body. The two-way communication can include transmitting and receiving electromagnetic radiation signals. The signals can be transmitted with a wavelength frequency in a range of approximately $1 \times 10^{-8}$ to $1 \times 10^{-1}$ Hz. The electromagnetic radiation signals can include infrared, visible light, radio waves, microwaves, ultraviolet, X-rays, gamma rays, ultrasonic signals or combinations thereof. The electromagnetic radiation signals can further travel through the body with minimal interference from the surrounding tissues or organs. The signals can measure blood pressure, ECG, heart rate, body temperature, glucose levels, gene and protein changes, local cellular changes that reflect systemic disease or change in health status or combinations thereof. The signals can be transmitted to an external receiver. The receiver can compare the signal to a reference signal to diagnose the disease or condition. The receiver can decode the signal to trigger an event. The event may include adjusting the patient's medical treatment.

In accordance with an example embodiment of the present invention, a chamber for use in monitoring physiological changes in the patient is disclosed. The chamber can include a body adapted to being situated within a secured to a vessel for implantation with a patient's body; an opening within the body; and a biologic component situated within the body comprising a cell layer having cells pre-positioned on or in the device prior to implantation, wherein said pre-positioned cells are adapted to respond to a physiological signal from a patient.

According to aspects of the present invention, the body can be tubular, rectangular, square, or any other shape. The body can be made from plastic, stainless-steel, polyamide, Teflon, polymers, or other synthetic or biological materials. The body can be made from one piece of material. The body can be made from two pieces of material secured together. The body can have at least one opening.

In accordance with yet further aspects of the present invention, the biologic component can be situated within the opening. The biologic component can further include a first membrane and a second membrane on either side of the biologic component. The first membrane can be non-porous. The first membrane can be made from glass. The second membrane can be porous that allows for select fluid and nutrients to pass to the cell layer. The opening can have wall on one side to secure the cell layer within the biologic component. The wall can have angled sides.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to an implantable device suitable for monitoring physiological changes within the body.

FIG. 1 through FIG. 9, wherein like parts are designated by like reference numerals throughout, illustrate an example embodiment or embodiments of an implantable biosensor suitable for monitoring physiological changes within the body, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Figure 1:
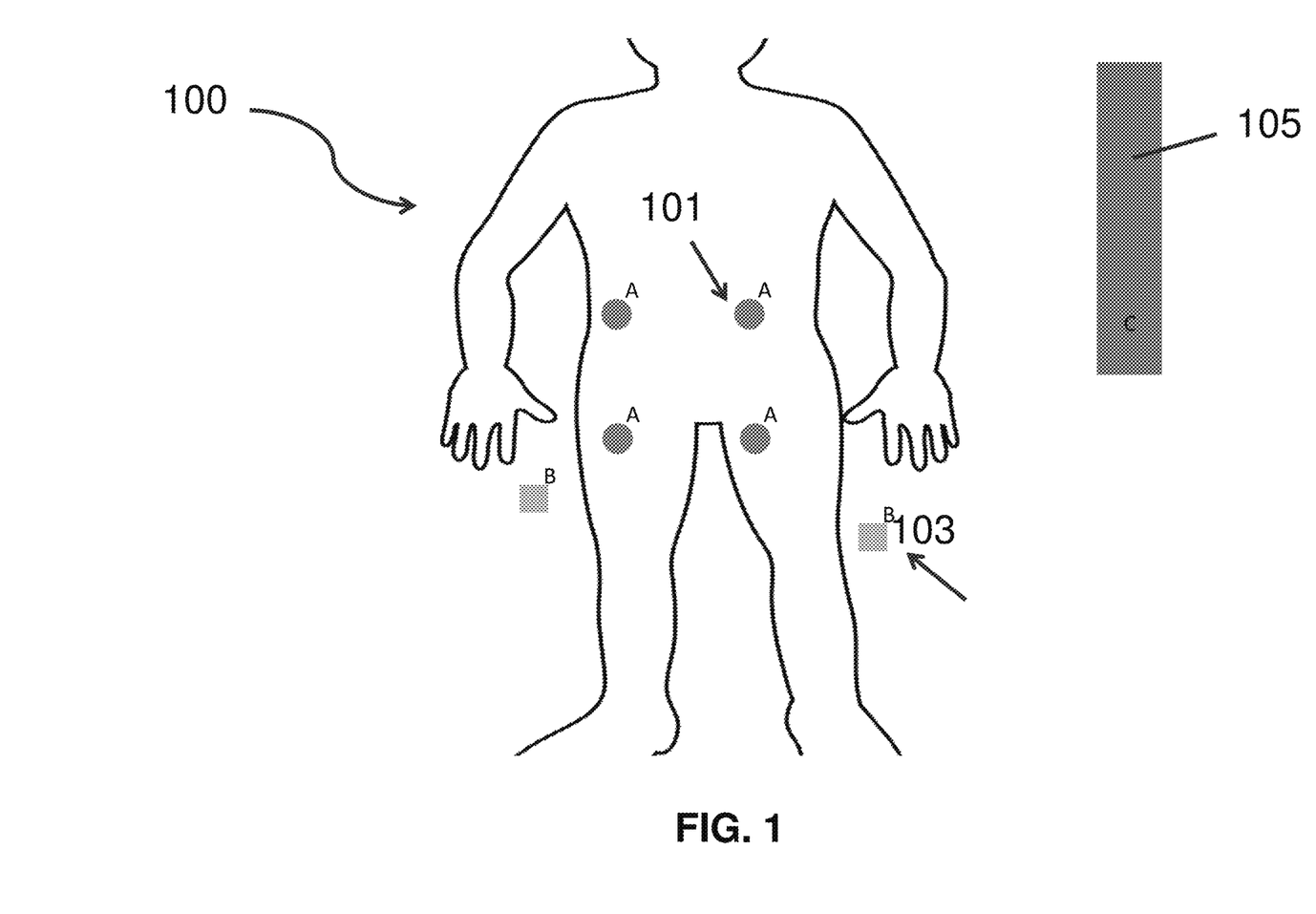
FIG. 1 is a drawing of an intra-body communication (IBC) system in accordance with an embodiment of the present invention.
Figure 2:
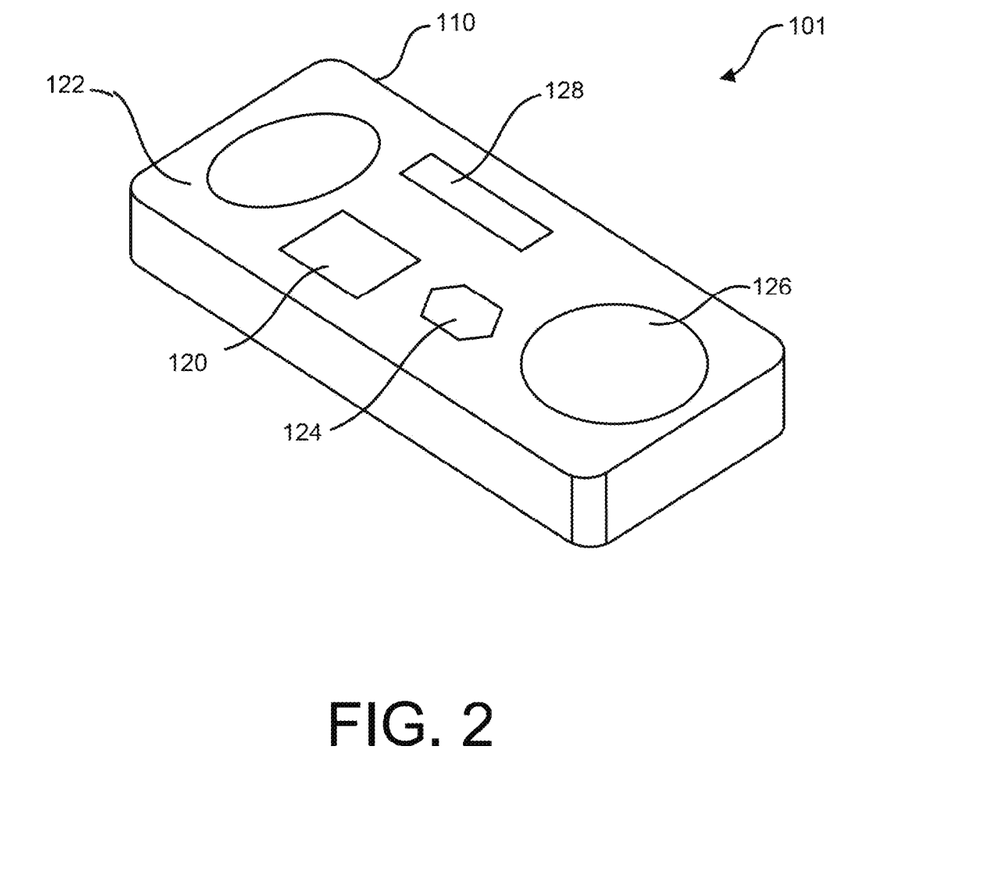
FIG. 2 is a photograph of an implantable device in accordance with an embodiment of the present invention.

As FIG. 1 illustrates, embodiments of an intra-body communication system 100 for use in monitoring physiological changes in the patient may comprise implantable devices 101, e.g., biosensors, for monitoring physiological changes within the body. As used herein, "intra-body communication" may refer to internal communication within a single mammalian body. However, sensors and components can be internally or externally to the individual. In one embodiment, the intra-body communication system 100 may comprise a first device 101 that produces a signal and a second device 103 spaced apart from the first device 101 for receiving the signal. In an embodiment, the first device 101 can monitor the integrated biologic tissue (biopsied and grown cells) and notice if there is a change in electrical activity of the cell, increased contraction or stretch activity, or metabolic activity as it responds to the physiologic signal of interest. In one embodiment, the direction of the signals is reversed. In one embodiment, both the first device 101 and the second device 103 are situated within the body. In another embodiment, only one of the components is external to the individual while the other is internal in the body. For instance, the first device 101 is internal in the body while the second device 103 is external to the body. In another embodiment, there may be any number devices implanted within the body or situated external to the body. The first device 101 may be the same or substantially the same as that described in U.S. Pat. Nos. 8,024,020; 8,849,416; 8,938,300 and U.S. patent application Ser. No. 13/212,804 all of which are hereby incorporated by reference.

In an embodiment, the first device 101 may include a vessel 110 adapted to being implanted within a patient's body. By "patient" or "subject" or "individual" or "animal" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on. The vessel 110 may be placed anywhere in the body and may be placed in direct contact with blood, or within other tissue such as adipose (fat) tissue, muscle, or specific organs including the spine and nervous system. In an embodiment, the vessel 110 is adapted to being implanted in each of a intravascular, extravascular, and perivascular space within the patient's body. As such, the vessel 110 can have any suitable shape and size. The vessel 110 may be oval, tubular, rectangular, square, pentagonal, hexagonal, or any other shape as long as the vessel 110 is able to be implanted within a patient's body. To prevent sharp edges or obstruction points to tissue or surrounding materials as they are engaged and moved, the edges of the tubes may be radiused or chamfered. The vessel 110 can be constructed of any materials suitable to form a structure, such as stainless steel, plastic, polyamide, Teflon, polymers, ceramic, or other synthetic or biological materials, such as, but not limited to, cartilage. In one embodiment, the materials have sufficient stiffness to maintain their own respective column and are able to increase the flexural rigidity of the probe to which they have been applied to.

This first device 101 does not require permanent long lead electrodes to be placed in the body tissue or vascular system. By combining cellular biologic sensors with microcircuitry, and eliminating the need for a lead, the first device 101 is small and can be placed in areas that are not accessible by chronic lead placement techniques. In addition, the device can have a wire that networks together multiple devices, though networking can also be wireless. The device can be placed transvenous as well as subcutaneous and/or within organs such as brain, gastrointestinal tract and central nervous system.

In an embodiment, the vessel 110 may include a cavity 112. The cavity 112 may be capable of holding a chamber 120 for use in monitoring physiological changes in the patient. In an embodiment, the cavity 112 may be any size or shape appropriate for holding the chamber 120. The cavity 112 may be tubular, rectangular, square, pentagonal, hexagonal, or any other shape.

Figure 3A:
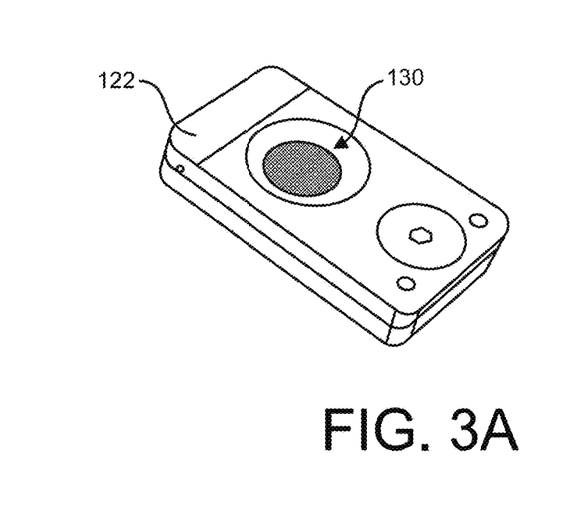
FIG. 3A, FIG. 3B, and FIG. 3C are perspective views of an implantable device in accordance with an embodiment of the present invention.
Figure 3B:
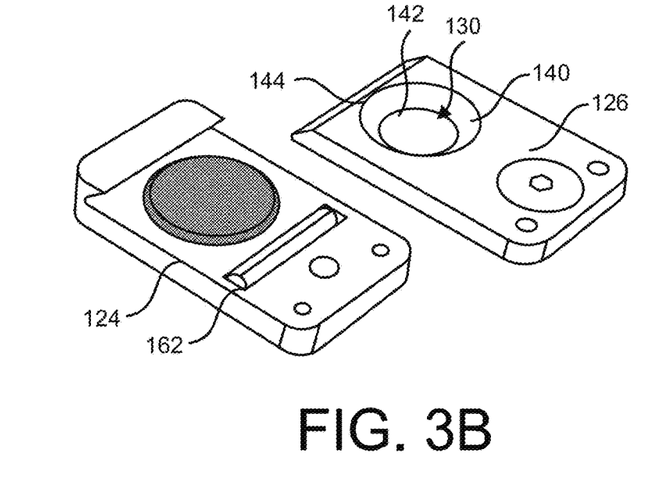
Figure 3C:
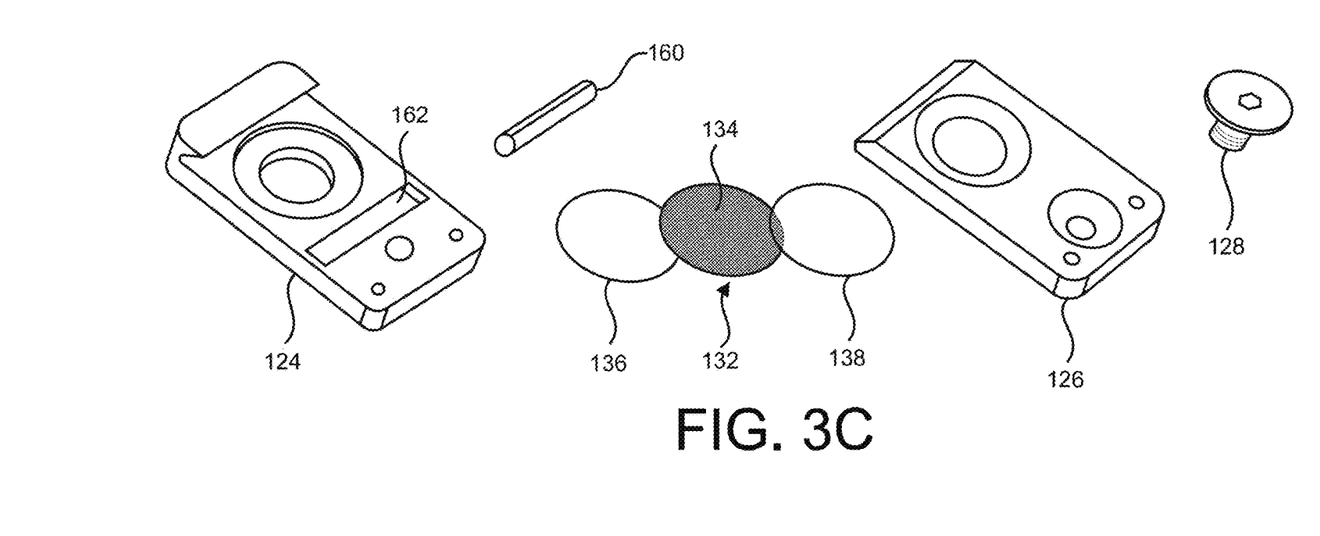
Figure 4:
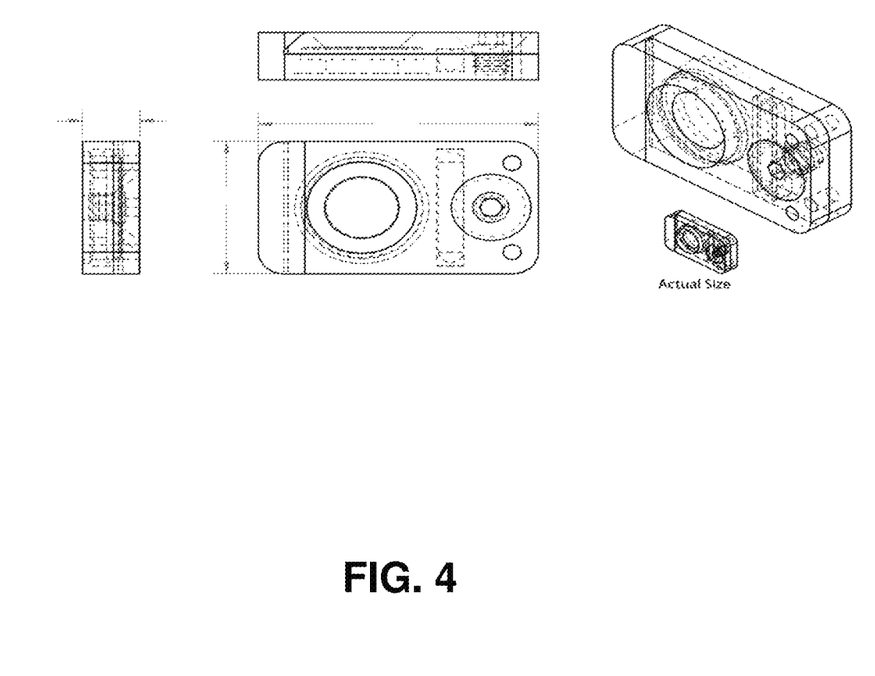
FIG. 4 is a drawing of an implantable device in accordance with an embodiment of the present invention.
Figure 5A:
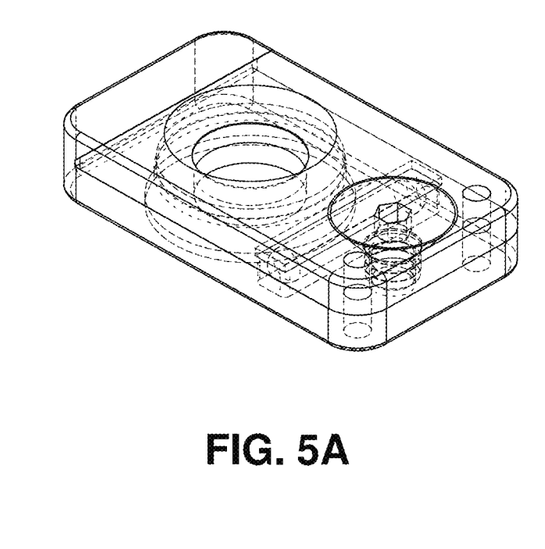
FIG. 5A and FIG. 5B are drawings of an implantable device in accordance with an embodiment of the present invention.
Figure 5B:
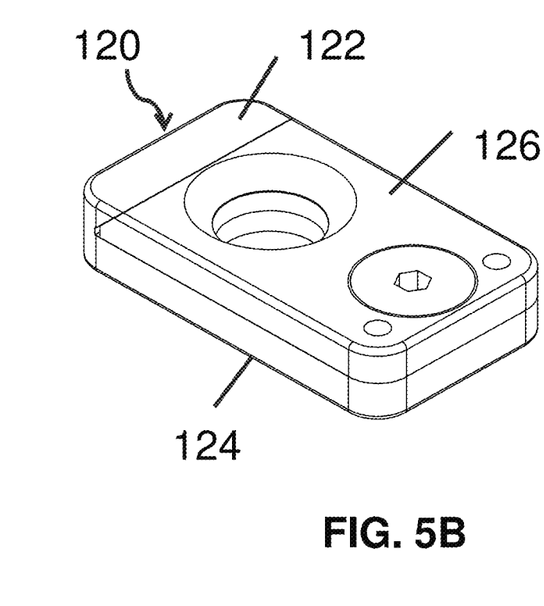

FIG. 3, FIG. 4, and FIG. 5 show various embodiments of chamber 120. As shown in FIG. 3A, the chamber 120 may include a body 122 capable of being secured to the cavity 112 of the vessel 110. The body 122 of chamber 120 may be permanently secured to the cavity 112 of the vessel 110 or it may be removable. To fit within the cavity 112 of the vessel 110, the body 122 of chamber 120 may be tubular, rectangular, square, pentagonal, hexagonal, or any other shape. The body 122 of chamber 120 can be constructed of any materials suitable to form a structure, such as stainless steel, plastic, polyamide, Teflon, polymers, ceramic, or other synthetic or biological materials, such as, but not limited to, cartilage. In an embodiment, the body 122 may range in length from about 0.40 mm to about 0.80 mm. As shown in FIG. 4, the body 122 may be about 0.663 mm in length. In an embodiment, the body 122 may range in width from about 0.10 to about 0.50 mm. As shown in FIG. 4, the body 122 may be about 0.375 mm in width. In an embodiment, the body 122 may range in height from about 0.05 mm to about 0.20 mm. As shown in FIG. 4, the body 122 may be about 0.135 mm in height. As used herein, the term "about" or "approximately" refers to a variation of 10% from the indicated values (e.g., 0.40, 0.80, etc.), or in case of a range of values, means a 10% variation from both the lower and upper limits of such ranges. For instance, "about 0.40 mm" refers to a range of between 0.36 mm and 0.44 mm.

FIG. 3, FIG. 5, FIG. 6, and FIG. 7 show various embodiments of body 122. As shown in FIG. 3B and FIG. 3C, body 122 may be made from two pieces of material capable of being secured to one another. In an embodiment, body 122 is made from a main enclosure 124 and a lid 126 which can be secured together using a fastener 128. It should further be appreciated by one skilled in the art that the body 122 may be made from one piece of continuous material or more than two pieces of material.

Figure 6A:
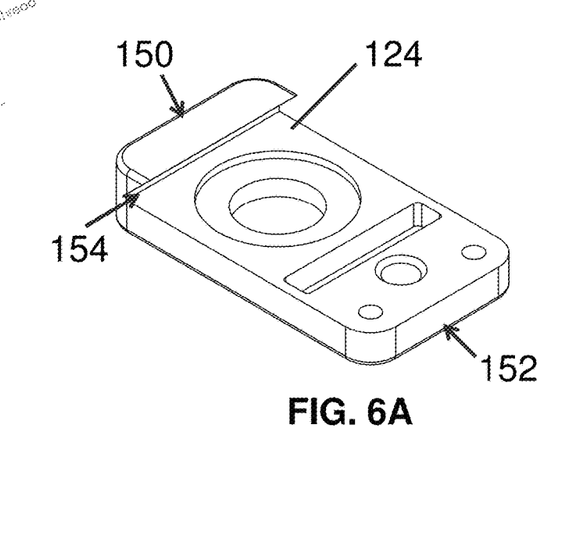
FIG. 6A, FIG. 6B, FIG. 6C, and FIG. 6D are drawings of an implantable device in accordance with an embodiment of the present invention.
Figures 6B, 6C:
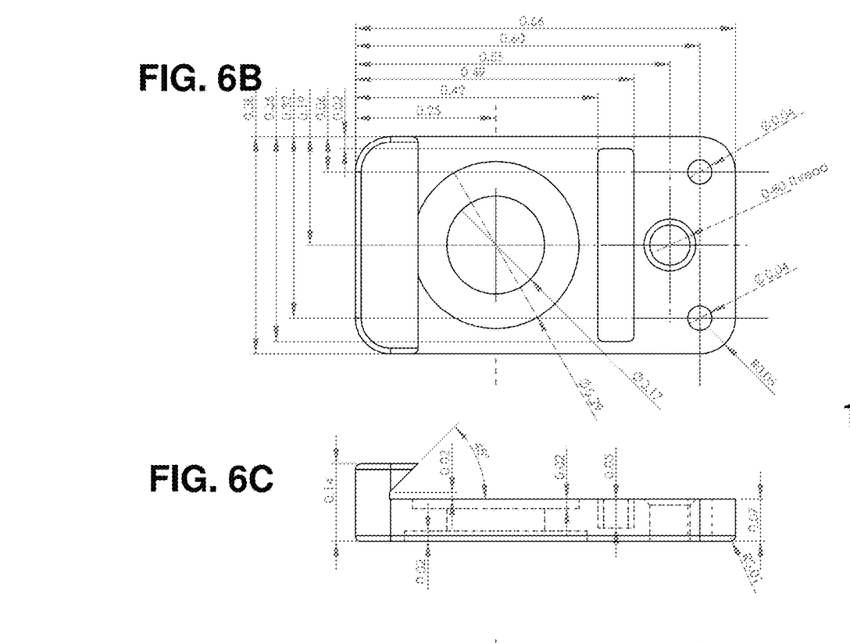
Figure 6D:
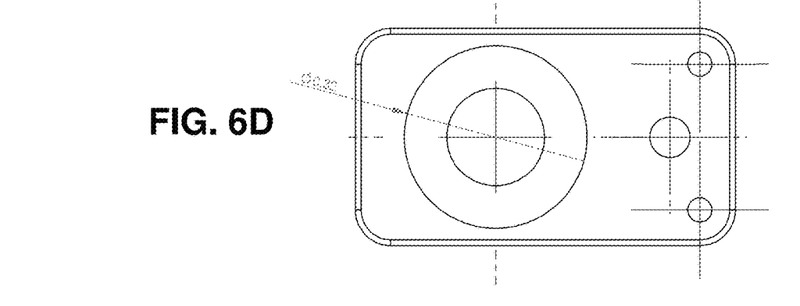

FIG. 6A, FIG. 6B, FIG. 6C, and FIG. 6D provide various dimensions of the main enclosure 124 in accordance with one embodiment of the present invention. In an embodiment, the main enclosure 124 may range in length from about 0.40 mm to about 0.80 mm. As shown in FIG. 6B, the main enclosure 124 may be about 0.66 mm in length. In an embodiment, the main enclosure 124 may range in width from about 0.10 to about 0.50 mm. As shown in FIG. 6B, the main enclosure 124 may be about 0.38 mm in width. In an embodiment, the main enclosure 124 may range in height from about 0.05 mm to about 0.20 mm. As shown in FIG. 6C, the main enclosure 124 may be about 0.14 mm in height on the first end 150 and about 0.07 mm in height on the second end 152. The first end 150 may further include a lip 154 for securing the lid 126.

Figures 7A, 7B, 7C, 7D:
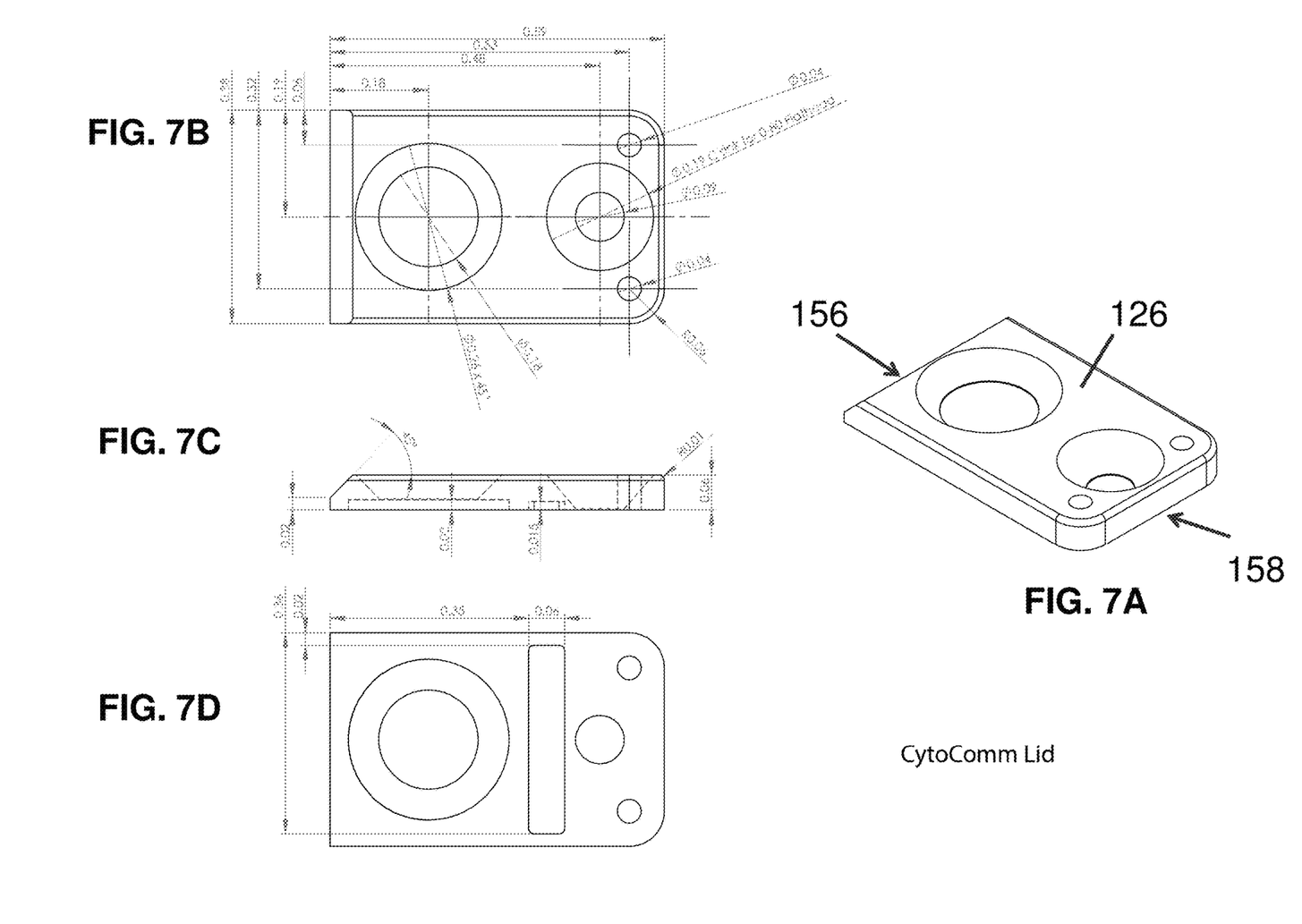
FIG. 7A, FIG. 7B, FIG. 7C, and FIG. 7D are drawings of an implantable device in accordance with an embodiment of the present invention.

FIG. 7A, FIG. 7B, FIG. 7C, and FIG. 7D provide various dimensions of the lid 126 in accordance with one embodiment of the present invention. In an embodiment, the lid 126 may range in length from about 0.40 mm to about 0.80 mm. As shown in FIG. 7B, the lid 126 may be about 0.59 mm in length. In an embodiment, the lid 126 may range in width from about 0.10 to about 0.59 mm. As shown in FIG. 7B, the lid 126 may be about 0.38 mm in width. In an embodiment, the lid 126 may range in height from about 0.02 mm to about 0.15 mm. As shown in FIG. 7C, the lid 126 may be about 0.02 mm in height on the first end 156 and about 0.06 mm in height on the second end 158. The first end 156 of the lid 126 is designed to fit securely into the lip 154 of the main enclosure 124.

As illustrated in FIG. 3A, the chamber 120 may include at least one opening 130 within the body 122. The opening 130 may be circular, rectangular, square, pentagonal, hexagonal, or any other shape. In one embodiment, the opening 130 is circular. The opening 130 may be any size appropriate for the chamber 120. In an embodiment, the diameter of the opening 130 ranges from about 0.10 mm and about 0.40 mm. As shown in FIG. 6B, the diameter is about 0.17 mm in diameter.

In an embodiment, the chamber 120 may include a biologic component 132 situated within the opening 130 in the body. In an embodiment, the biologic component may include cells 134 pre-positioned on or in the device prior to implantation. The pre-positioned cells 134 may be adapted to respond to a physiological signal from a patient. In one embodiment, the cells 134 may be from the target site. In another embodiment, the cells 134 may be from other sites.

The cells 134 may be placed in one layer, two layers, or multiple layers. Furthermore, the cells may be placed within three-dimensional (i.e., multi-layered) matrices and not limited to such a layer on a two-dimensional plate. The cells 134 are placed so that the cells 134 have a thickness of generally no more than about 0.54 mm so that the cells receive ample nutrients including oxygen exposure.

The cells 134 are cells of interest (such as, but not limited to, cardiac, vascular, gastrointestinal, bone, tissue, or cartilage, depending on the application) which are cultured or otherwise obtained from the patient and grown in an implantable chamber. The internal environment and architecture of the chamber is optimized to support the specific cells of interest and may include but not limited to, natural and synthetic matrix materials used for scaffolding and support of cells 134. Since the cells are cells of interest from the patient, they are able to survive once implanted. The chamber 120 is a biocompatible structure that allows the healthy growth and adhesion of cells. Although synthetic and/or naturally occurring substances are preferred, any substance can be used that has biocompatibility with the target cells and maintains cellular architecture intact while allowing cells to grow and live within its environment.

The cells 134 are selected based on their ability to detect and respond to the physiologic signal of interest. For example, if a response to circulating chemical messengers such as catecholamines is required information, then skeletal muscle may be used. Accordingly, those cells eliminate the need for a separate sensor to detect the desired chemical messenger. In this setting, the muscle is biopsied from the arm or leg and placed into an environment that allows separation of the cells in an atraumatic fashion so as to minimize damage. The cells are then grow onto the device. The site of growth includes direct contact with an array of electrodes or Micro-electromechanical devices. The electrode array interface may be in a single plane or the electrodes distributed within a three-dimensional architecture so that the cells are in direct contact with a variety of electrodes. When the cell have matured and attached themselves to the electrode/sensor circuitry/MEMs, then the device is prepared for implantation within the same person from whom the cells were obtained. Alternatively the cells may be from another human or non-human source and produced in such as way to be compatible with the person in whom it is implanted. This minimizes scar formation and rejection.

In this scenario, the cells 134 respond to increase in catecholamines by increasing their frequency of firing as well as strength of contraction, which is measured by a shear stress recording sensor, pressure via pressure transducer, and the rate of change of the mechanical conformational changes. The change in shear stress/pressure and/or electrical activity (amplitude and frequency) can be detected. The electrical activity is also recorded if it is the desired signal or cellular response that is used as a marker. The first device 101 then transmits the detection to an external controller or may have its own controller that either stores and/or acts on the information by emitting an electrical stimulus to inhibit or stimulate the target organ in which the device is implanted. The data may also be wirelessly communicated, for example using ultrasonic sound, to another networked implanted or external device that then performs the intervention that may consist of electrical stimulation, or trigger an infusion of a substance by an implanted or external pump.

Within the chamber 120, the cells 134 are situated between a first 136 membrane and a second membrane 138 as shown in FIG. 3C. The first membrane 136 and second membrane 138 function to keep the cells 134 positioned in one place and prevent them from being distorted. In one embodiment, the first membrane 136 is non-porous. The first membrane 136 is positioned adjacent to or abutting the vessel 110 and provides an interface between the vessel 110 and the cells 134 it contacts. In one embodiment, the first membrane 136 is made of glass. The second membrane 138 is positioned adjacent to the human body and provides an interface between the human body and the cells 134 it contacts. In contrast to the first membrane 136, the second membrane 138 may be porous to allow for select fluid and nutrients to pass to the cells 134.

To maintain the positioning of the cells 134 between the first membrane 136 and second membrane 138, the opening of the chamber 120 may be in the form of a crater, as shown in FIG. 3A and FIG. 3B. In one embodiment shown in FIG. 3B, the crater shape may include walls 140 that extend from the base 142 of the crater to the top 144 of the crater. At the base 142 of the crater is the second membrane 138 which contains the layer of cells 134. The wall 140 acts to secure the cell layer within the biologic component and prevent distortion or migration of the cells. In one embodiment, the base 142 of the crater has a smaller diameter than the top 144 of the crater. In another embodiment, the base 142 of the crater has the same or substantially the same diameter as the top 144 of the crater. In one embodiment, the wall 140 may have angled sides in relation to the biologic material 132. In one embodiment, the sides of the wall 140 may be angled between about 30 degrees and 90 degrees. In one embodiment, the sides of the wall 140 may be angled at about 45 degrees.

In addition, an optional coating may be applied to the outer surface of cells 134 or to the first membrane 136 or second membrane 138. The coating may inhibit the formation of scar tissue or fibrotic growth over the first device 101. In addition, a coating may include substances to promote growth of blood vessels around the device to enhance or optimize contact with blood/fluid borne signals. In another embodiment, the coating may be a drug-eluting coating which delivers drug to surrounding tissue at predetermined rates. In an embodiment, the coating may is GORE-TEX®, which is manufactured by Guidant and is suitable for high voltage applications, but can also be steroids or a combination of steroids and GORE-TEX®. Steroids dilute over time and eventually disappears.

Figure 8A:
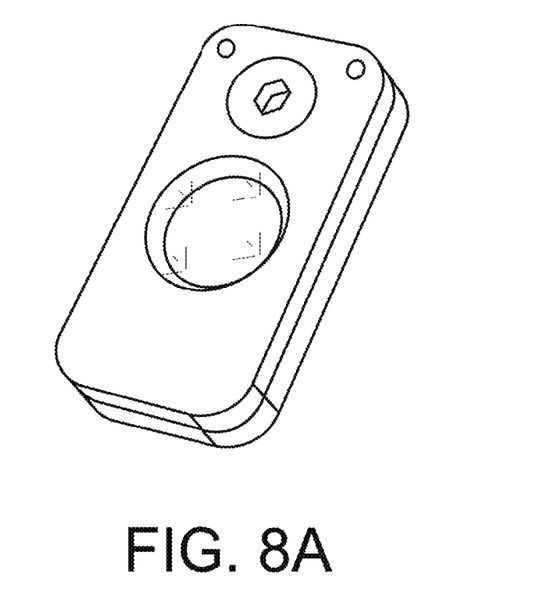
FIG. 8A and FIG. 8B are photographs of an implantable device in accordance with an embodiment of the present invention.
Figure 8B:
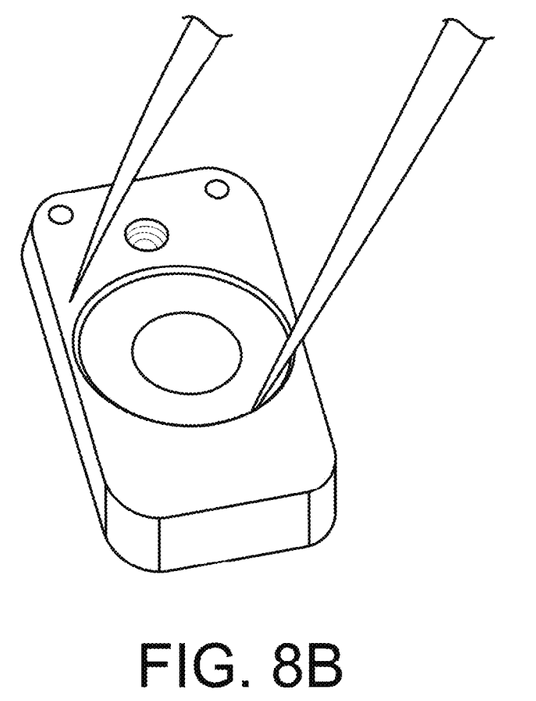

In an embodiment, the first device 101 may further include an electronic component 114. In an embodiment, the electronic component may include a light source (not shown) for shining light onto the cells 134 through the first membrane 136 thereby causing certain cells 134 to emit light as shown in FIG. 8A. In FIG. 8A, an excitation signal in the form of light is emitted by an excitation emitter (not shown) that enters the cells 134. The cells 134 have surface receptors that are integral to the membrane proteins of the cell. When a signal (e.g., light) interacts with the receptors, they form a triggering mechanism that stimulates a signaling response that may also include DNA/RNA response that, in turn, causes a protein to be synthesized by the cells 134. It may also trigger direct protein conformational changes independent of protein synthesis that can be detected. That protein has certain physical properties, including the ability to fluoresce upon absorption of certain wavelengths of light. The more protein present in the cells 134, the higher the fluorescence intensity. In an alternate embodiment, a detection protein, like green fluorescent protein (GFP) from jellyfish, may be attached to the protein (other detection substances may also be used). In an alternate embodiment, an intracellular dye may also be used instead of GFP.

To detect and/or decode light emitted from the cells 134, the electronic component 114 of the first device 110 may further include a reader. The reader detecting and/or decoding light emitted from the cells 134 to monitor physiological changes in the patient. The cells 134 provide sensing and individual cellular responses that can be measured by the electronic component 114, such as pressure and deformation changes in cellular structure, photo-optical changes elicited by the cell. The ability to detect and measure these various cellular responses, the first device 101 provides a broad range of clinical application for which it can be used. The first device 101 such as that of the present invention can be individually tailored to measure different physiological changes in the patient.

The first device 101 may further include radio frequency identification (RFID) tag 160 for remotely storing and retrieving data. An RFD tag 160 is a small object, such as an adhesive sticker, that can be attached to or incorporated into the implantable device 110 of the present invention. As shown in FIG. 3B and FIG. 3C, the main enclosure 124 of the vessel 122 may include a slot 162 for housing the RFID tag 160. There are passive and active RFID tags. Passive RFID tags are small devices that are generally used at shorter range and for simpler tracking and monitoring applications than active tags. Passive tags generally act over ranges up to 3-5 meters, and a few hundred are typically readable simultaneously within three meters of a reader. Because they are powered by radio waves from RFID tag reader, passive tags do not use a battery. Therefore these devices are generally inexpensive and smaller than active tags, and can last long. Active RFID tags have a power source, such as a battery, and generally have longer range and larger memories than passive tags. For example, active tags generally act over ranges up to 100 meters, and thousands of tags are typically readable simultaneously within 100 meters of a reader. For more details on passive and active RFID tags, see http://RFID-Handbook.com, which is hereby incorporated by reference. It should be appreciated that any sort of identification tagging, including bar code or other electronic means, may also be used.

In an embodiment, the second device 103 may be the same or substantially the same as the first device 103. In another embodiment, the second device 103 may be different from the first device 103. For instance, the second device 103 may a pace maker, a glucose monitor pump, an insulin pump, a neurostimulator, a defibrillator or any other medical device that can be implanted within or carried on a person.

Figure 9:
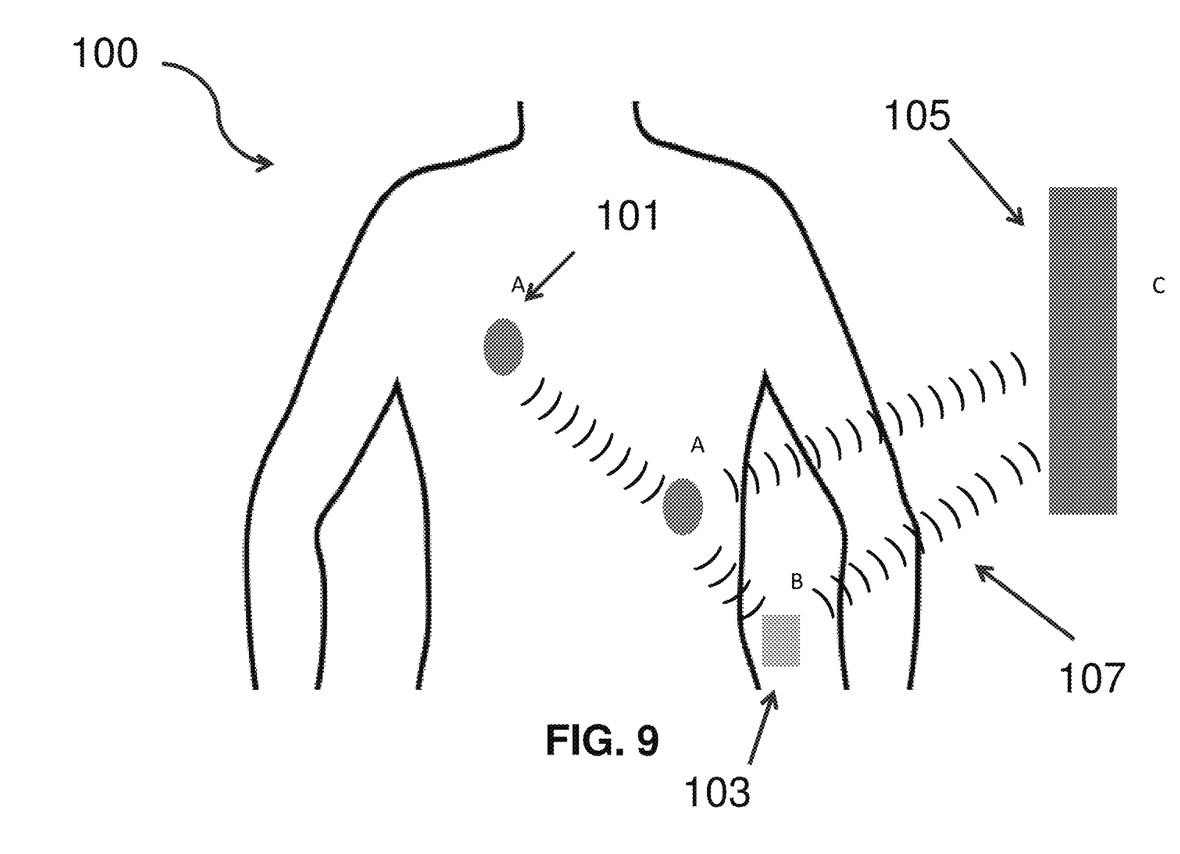
FIG. 9 is a drawing of an intra-body communication (IBC) system in accordance with an embodiment of the present invention.

As shown in FIG. 9, the first device 101 and second device 103 are capable of engaging in a two-way communication through transmission of one of more signals 107 through at least a portion of the patient's body between the first device 101 and the second device 103. In an embodiment, the two-way communication includes transmitting and receiving signals. In accordance with an embodiment of the present invention, the signals may be electromagnetic radiation signals. In an embodiment, the electromagnetic radiation signals may include infrared, visible light, radio waves, microwaves, ultraviolet, X-rays, gamma rays, ultrasonic signals or combinations thereof.

In an embodiment, the electromagnetic radiation signals 107 may travel through the body with minimal interference from the surrounding tissues or organs. For instance, the electromagnetic radiation signals 107 may travel through muscles, organs such as lungs and the heart, bone, cartilage, or any other tissues in the body while experience minimal interference and/or loss in wavelength frequency. In an embodiment, it is expected that the loss in wavelength frequency will be less than 10%, less than 9%, less than 8%, less than 7%, less than 6%, less than 5%, less than 4%, less than 3%, less than 2%, or less than 1%. It should be appreciated that the amount of loss can vary based on a number of factors. For instance, the amount of loss can depend on the type of signal and/or the type of wavelength selected. In addition, the amount of loss may depend on the amount of absorption, diffusion and/or scatter. It should be appreciated by one skilled in the art, however, that the amount of loss will be minimal and will not impact the operation of the invention of the present application.

In embodiments, the signal is encoded using frequency and/or amplitude modulation. In this way, the signal 107 may carry data such as blood pressure, heart rate, ECG, body temperature, glucose levels, gene and protein changes, local cellular changes that reflect systemic disease or change in health status or other body parameters to receiver 105. In an embodiment, the electromagnetic radiation signals include infrared, ultrasonic signals, combinations thereof, or any other signals known in the art. In an embodiment, the electromagnetic radiation signals may have a wavelength frequency in a range of approximately $1 \times 10^{-8}$ to $1 \times 10^{-1}$ Hz. Of course, it should be appreciated to anyone skilled in the art that the wavelengths may vary.

After traveling through the body, the signal 107 can be transmitted to the receiver 105, as shown in FIG. 9, which then detects the signal 107. In addition, receiver 105 may decode or demodulate the signal 107 to receive the data encoded within the signal 107 and may compare the signal 107 to a reference signal to diagnose the disease or condition. In response to the detected signal 107, receiver 105 may initiate an action. The action can include adjusting the patient's medical treatment (i.e. drug delivery), activate an alarm, send information to the physician, etc.

Accordingly, it is envisioned that the disclosed intra-body communication system 100 may be used in numerous applications. In one embodiment, the intra-body communication system 100 may be used for drug release applications. For example, an internal drug dispensing device may be implanted within a patient. The receiver 105 may be coupled to the drug dispensing device. In response to a signal 107, the receiver 105 may instruct the drug dispensing device to release drugs into the body. Sensors may then detect the effectiveness of the drug and allow the user to trigger another dose release. Such systems may allow for patient targeted treatment. This may be particularly useful in chronically ill patients, such as diabetic patients or patients undergoing cancer treatment.

In another application, the implantable device 101 may be used in health monitoring. Similar to the above application, the receiver 105 may detect and decode the signal 107 and may store data on storage medium such as a flash card, hard drive, or other devices known to those of skill in the art and/or send the data to a base station, such as a computer, a smart phone, or cell phone. Depending on the complexity of the system setup the information may be forwarded directly to a physician's office or nurses station, first responders, or other qualified personnel who may then review the data and access the best possible treatment path forward.

In a further application, embodiments of the disclosed implantable device 101 could be used to diagnosis medical conditions. Currently, a health care professional may be able to diagnose conditions and diseases only after reviewing and analyzing data such as the results of blood work, x-ray, computed tomography or magnetic resonance imaging, etc. Without being limited to theory, it is believed that conditions or diseases may have distorted signal 107. In a healthy individual, the signal 107 may be transmitted differently than in an unhealthy individual. Using an embodiment of the disclosed system, differences in the signal 107 or rate of transmission may alert a health care professional of a possible injury, disease or condition.

The implantable device 110 of the present invention can also provide information for use by other medical devices, such as a cardiac ventricular assist device to alter its flows and parameters to maximize cardiac output. The implantable device 110 can alternatively be used to modulate blood pressure and central nervous system reflexes such as the baroreceptor reflex system from peripheral nervous system points or directly form the brain itself. It can also be used to predict events such as ventricular fibrillation or onset of seizure activity within the brain by detecting neuro-transmitter changes that can only be detected by biologic tissue.

The implantable device 110 of the present invention is able to stimulate tissue with a predetermined sub-threshold pacing and determine the response of the cells 134 to obtain data regarding the cells perception of the body's physiologic processes. For example, a cell may slightly increase electrical frequency of depolarization in response to an event, but the first device 101 may increase the sensitivity of the detection by stimulating the cell 132 and study the response of the cells 132 to the stimuli as a way of interpreting the signal. The stimulation triggers a response from the cells depending on the application. That evoked response provides information about the conditions being sensed by the cells.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall there between.

What is claimed is:

1. An implantable device for use in monitoring physiological changes in a patient, the device comprising:
    a vessel adapted to being implanted into any one of an intravascular space, an extravascular space, and a perivascular space, within the patient's body;
    a chamber situated within the vessel, the chamber comprising a biological component having a cell layer, and adapted to being secured to the vessel, wherein the cell layer comprises cells pre-positioned on or in the device prior to implantation, and wherein the pre-positioned cells are adapted to respond to a physiological signal from the patient by emitting fluorescence;
    a light source for shining light onto the cell layer, thereby causing certain cells within the cell layer to emit fluorescence, wherein the emitted fluorescence is an indication of blood pressure, ECG, heart rate, body temperature, gene and protein changes, local cellular changes that reflect systemic disease or change in health status, or combinations thereof; and
    a reader for detecting and/or decoding the emitted fluorescence from the cell layer to monitor physiological changes in the patient and for transmitting an electromagnetic radiation signal to an external receiver, wherein the electromagnetic radiation signal that is transmitted to the external receiver is selected from infrared, visible light, radio waves, microwaves, ultraviolet, X-rays, gamma rays, and combinations thereof, and wherein the external receiver detects and decodes the transmitted electromagnetic radiation signal, and in response, subsequently triggers an adjustment in drug delivery from a second device implanted within the patient's body, wherein the second device is capable of drug delivery.

2. The device of claim 1, wherein the vessel is tubular, rectangular, square, oval, pentagonal, or hexagonal.

3. The device of claim 1, wherein the chamber comprises a body adapted to being secured to the vessel.

4. The device of claim 3, wherein the body comprises plastic, stainless-steel, polyamide, Teflon, polymers, or other synthetic or biological materials.

5. The device of claim 3, wherein the body comprises one piece of material.

6. The device of claim 3, wherein the body comprises two pieces of material secured together.

7. The device of claim 1, wherein the chamber further comprises a first membrane and a second membrane on either side of the biologic component.

8. The device of claim 7, wherein the first membrane is a non-porous membrane on which the cell layer is pre-positioned.

9. The device of claim 7, wherein the first membrane comprises glass.

10. The device of claim 7, wherein the first membrane is adjacent to the light source.

11. The device of claim 7, wherein the second membrane is porous and allows fluid and nutrients to pass therethrough to the cell layer.

12. The device of claim 7, wherein the second membrane is distal to the light source.

13. The device of claim 1, wherein the device is adapted for wireless communication.

14. The device of claim 1, wherein the device is adapted for engaging in a two-way communication through transmission of one of more signals through at least a portion of the patient's body.

15. The device of claim 14, wherein the two-way communication includes transmitting and receiving electromagnetic radiation signals.

16. The device of claim 15, wherein the electromagnetic radiation signals include infrared, visible light, radio waves, microwaves, ultraviolet, X-rays, gamma rays, ultrasonic signals, or combinations thereof.

17. The device of claim 15, wherein the electromagnetic radiation signals travel through the body with minimal interference from the surrounding tissues or organs.

18. An implantable device for use in monitoring physiological changes in a patient, the device comprising:
    a vessel adapted to being implanted into any one of an intravascular space, an extravascular space, and a perivascular space, within the patient's body;
    a chamber situated within the vessel, the chamber comprising a biological component having a cell layer, and adapted to being secured to the vessel, wherein the cell layer comprises cells pre-positioned on or in the device prior to implantation, and wherein the pre-positioned cells are adapted to respond to a physiological signal from the patient by emitting fluorescence;
    a light source for shining light onto the cell layer, thereby causing certain cells within the cell layer to emit fluorescence, wherein the emitted fluorescence is an indication of blood pressure, ECG, heart rate, body temperature, gene and protein changes, local cellular changes that reflect systemic disease or change in health status, or combinations thereof; and
    a reader for detecting and/or decoding the emitted fluorescence from the cell layer to monitor physiological changes in the patient and for transmitting an electromagnetic radiation signal, having a wavelength frequency, to an external receiver, wherein the electromagnetic radiation signal that is transmitted to the external receiver is selected from infrared, visible light, radio waves, microwaves, ultraviolet, X-rays, gamma rays, and combinations thereof, wherein the electromagnetic radiation signal travels through the body with minimal interference from the surrounding tissues or organs, such that the loss in the wavelength frequency is less than 10%; and wherein the external receiver detects and decodes the transmitted electromagnetic radiation signal, and in response, subsequently triggers an adjustment in drug delivery from a second device implanted within the patient's body, wherein the second device is capable of drug delivery.

19. The device of claim 18, wherein the vessel is tubular, rectangular, square, oval, pentagonal, or hexagonal.

20. The device of claim 18, wherein the chamber further comprises a first membrane and a second membrane on either side of the biologic component.

21. The device of claim 20, wherein the first membrane is a non-porous membrane on which the cell layer is pre-positioned.

22. The device of claim 20, wherein the first membrane comprises glass.

23. The device of claim 20 wherein the first membrane is adjacent to the light source.

24. The device of claim 20, wherein the second membrane is porous and allows fluid and nutrients to pass therethrough to the cell layer.

25. The device of claim 20, wherein the second membrane is distal to the light source.

26. The device of claim 18, wherein the chamber comprises plastic, stainless-steel, polyamide, Teflon, polymers, or other synthetic or biological materials.

27. The chamber of claim 18, wherein the chamber comprises one piece of material.

28. The chamber of claim 18, wherein the chamber comprises two pieces of material secured together.

29. The device of claim 18, wherein the device is adapted for wireless communication.

30. The device of claim 18, wherein the device is adapted for engaging in a two-way communication through transmission of one of more signals through at least a portion of the patient's body.

31. The device of claim 30, wherein the two-way communication includes transmitting and receiving electromagnetic radiation signals.

32. The device of claim 18, further adapted to stimulate surrounding tissue with a predetermined sub-threshold pacing and determine the response of the cells in the cell layer.

33. The device of claim 18, wherein the external receiver detects and decodes a an unhealthy condition or disease from a distortion of the transmitted electromagnetic radiation signal.

* * * * *